United States Patent
Mitsuka et al.

[11] Patent Number: 5,980,881
[45] Date of Patent: *Nov. 9, 1999

[54] MEDICAMENT FOR PREVENTIVE AND/OR THERAPEUTIC TREATMENT OF HYPERPHOSPHATEMIA

[75] Inventors: Masayuki Mitsuka; Hiroshi Shimada; Mizue Kawai, all of Kanagawa, Japan

[73] Assignee: Mitsubishi Chemical Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/812,129

[22] Filed: Mar. 5, 1997

[30] Foreign Application Priority Data

Mar. 5, 1996 [JP] Japan .................................. 8-047765

[51] Int. Cl.$^6$ .................................................. A61K 31/785
[52] U.S. Cl. ............................................................ 424/78.1
[58] Field of Search ................................ 424/78.1, 78.14, 424/78.16

[56] References Cited

U.S. PATENT DOCUMENTS

| | | | |
|---|---|---|---|
| 4,412,011 | 10/1983 | Kihara et al. | 521/38 |
| 5,380,522 | 1/1995 | Day | 424/78.08 |
| 5,447,726 | 9/1995 | Nomura | 424/464 |
| 5,496,545 | 3/1996 | Holmes-Farley et al. | 424/78.11 |

FOREIGN PATENT DOCUMENTS

| | | |
|---|---|---|
| 0 098 884 | 1/1984 | European Pat. Off. . |
| 0 157 410 | 10/1985 | European Pat. Off. . |
| 56-150017 | 11/1981 | Japan . |
| WO94/27619 | 12/1994 | WIPO . |
| WO95/05184 | 2/1995 | WIPO . |
| WO96/21454 | 7/1996 | WIPO . |

OTHER PUBLICATIONS

Hagmaier et al., Helv. Chis. Acta., vol. 48, No. 3–4 (1981) pp. 421–424.
Burt et al., Uremia Invest., vol. 9, No. 1 (1986), pp. 35–44.
Grynpas et al., Life Support Syst., vol.; 4, No. suppl. 2 (1986) pp. 276–278.
Burt et al., J. Pharma. Sci., vol. 76, No. 5 (May 1987) pp. 379–383.

*Primary Examiner*—Peter F. Kulkosky
*Attorney, Agent, or Firm*—Wenderoth, Lind & Ponack, L.L.P.

[57] ABSTRACT

A medicament for preventive and/or therapeutic treatment of hyperphosphatemia which comprises a pharmaceutically acceptable anion exchange resin such as a 2-methylimidazole/epichlorohydrin copolymer, cholestyramine resin, or colestipol. The medicament is orally available and has lowering effect on blood phosphate concentration and reducing effect on urinary phosphate excretion, and is useful for the treatment of conditions caused by hyperphosphatemia including renal dysfunction and the like.

4 Claims, 7 Drawing Sheets

MEDICAMENT FOR PREVENTIVE AND/OR THERAPEUTIC TREATMENT OF HYPERPHOSPHATEMIA

BACKGROUND OF THE INVENTION

1. Field of the Invention

The present invention relates to a medicament for preventive and/or therapeutic treatment of hyperphosphatemia. More specifically, the present invention relates to a medicament for preventive and/or therapeutic treatment of hyperphosphatemia which comprises a pharmaceutically acceptable anion exchange resin as an active ingredient.

2. Background Art

In patients of renal dysfunction, insufficiency of urinary phosphate excretion is observed. In the early stage of renal failure, a renal compensatory mechanism acts to keep phosphate homeostasis, and a temporary increase of phosphate excretion is observed due to the depression of phosphate re-absorption induced by the increase of PTH (parathyroid hormone). However, the homeostasis cannot be maintained because of progression of renal pathological conditions and renal hypofunction. As a result, hyperphosphatemia due to the decrease of phosphate excretion and a marked increase of PTH may arise. The accumulated phosphate causes, as direct actions, decrease of blood calcium, acceleration of PTH production/secretion, heterotopic calcification, and renal osteoparatrophy due to the depression of vitamin D activation. As indirect actions through high PTH level, it causes central and peripheral nervous disorders, myocardial disorders, hyperlipidemia, carbohydrate metabolic disorders, itch, dermal ischemic ulcer, anemia, tendon rupture, genital dysfunction, myopathy, growth retardation, cardiac conduction disturbance, pulmonary inflation disorder arterial sclerosis, and immune deficiency. In addition, it is also known that phosphate is an uremic substance and is involved directly or indirectly in complications of renal failure (Jin to Toseki, "Kidney and Dialysis", 37, 2:321, 1994).

When dialysis treatment is finally applied to patients of renal failure, the aforementioned pathologic conditions and complications are maintained, if homeostasis of phosphate cannot be sustained. Therefore, treatment of hyperphosphatemia is essential for patients of renal failure under or before the treatment of dialysis. For the treatments of hyperphosphatemia, 1) diet therapy, or 2) orally available phosphate adsorbent is currently applied.

Low protein food is used for the diet therapy. However, the effects of decrease of blood phosphate level are sometimes inefficient because its prolonged intake is limited and a certain level of protein intake cannot be avoided.

As orally available phosphate binders, mainly three types as set forth below are currently used. 1) Aluminum preparation (aluminum hydroxide): This preparation has problems of aluminum encephalopathy and aluminum osteopathy due to aluminum absorption. 2) Calcium preparation (calcium carbonate, calcium acetate): This preparation has weaker adsorbability compared to aluminum and requires higher dosage. In addition, there is also a problem that hypercalcemia may be caused due to calcium absorption. 3) Magnesium preparation (magnesium carbonate). This preparation has a problem that hypermagnesemia may be caused like the calcium preparation.

Therefore, each of the therapeutic treatments now available for hyperphosphatemia has the expected problematic actions, and cannot be applied for a prolonged period of time. Any improved therapeutic drug for hyperphosphatemia has not yet been discovered to date.

Japanese Patent Unexamined Publication (KOKAI) No. 56-150017/1981, European Patent Publication No. 98,884/A1, U.S. Pat. No. 4,412,011, and European Patent publication No. 157,410/A1 disclose that certain anion exchange resins have cholesterol-lowering activities. In addition, a cholesterol depressant comprising an anion exchange resin, i.e., cholestyramine resin, is sold by Bristol Myers Squibb Co. (trade name: Questran), and a cholesterol depressant comprising an anion exchange resin, i.e., colestipol hydrochloride, from The Upjohn Co. (trade name: Colestid). However, as far as the inventors of the present invention know, it has not reported to date that these anion exchange resins have phosphate ion-adsorbing activities, and furthermore, they have lowering activities on blood phosphate concentrations and reducing activities on urinary phosphate excretion.

SUMMARY OF THE INVENTION

The inventors of the present invention conducted various researches to solve the foregoing problems. As a result, they found that pharmaceutically acceptable anion exchange resins have phosphate adsorbing activities, lowering activities on blood phosphate concentrations, and reducing activities on urinary phosphate excretion. They also found that the resins are free from the aforementioned problems due to undesired absorption which may be caused by the aluminum, calcium, and magnesium preparations currently used for preventive and/or therapeutic treatment of hyperphosphatemia. The present invention was achieved on the basis of these findings.

The present invention thus provides a medicament for preventive and/or therapeutic treatment of hyperphosphatemia which comprises a pharmaceutically acceptable anion exchange resin.

According to preferred embodiments of the present invention, the above-defined preventive and/or therapeutic medicament wherein the anion exchange resin is selected from the group consisting of a 2-methylimidazole/epichlorohydrin copolymer, cholestyramine resin, and colestipol; the above-defined preventive and/or therapeutic medicament wherein the anion exchange resin is selected from the group consisting of a 2-methylimidazole/epichlorohydrin copolymer and cholestyramine resin; the above-defined preventive and/or therapeutic medicament wherein the anion exchange resin is a 2-methylimidazole/epichlorohydrin copolymer; the above-defined preventive and/or therapeutic medicament wherein the efficacy is based on lowering activity on blood phosphate concentration; the above-defined preventive and/or therapeutic medicament wherein the efficacy is based on reducing activity on urinary phosphate excretion; the above-defined preventive and/or therapeutic medicament which is applied to hyperphosphatemia accompanied with renal dysfunction; the above-defined preventive and/or therapeutic medicament wherein the medicament is orally available; and the above-defined preventive and/or therapeutic medicament wherein the anion exchange resin has cholesterol lowering activity.

According to another aspect of the present invention, a phosphate binder comprising a pharmaceutically acceptable anion exchange resin; the above-defined phosphate binder which is selected from the group consisting of a 2-methylimidazole/epichlorohydrin copolymer, cholestyramine resin, and colestipol; the above-defined phosphate binder which is selected from the group consisting of a 2-methylimidazole/epichlorohydrin copolymer and cholestyramine resin; and the above-defined phosphate binder which is a 2-methylimidazole/epichlorohydrin copolymer.

DETAILED EXPLANATION OF THE INVENTION

Explanation of the Preferred Embodiments

The active ingredients of the medicaments of the present invention for preventive and/or therapeutic treatment of hyperphosphatemia are not particularly limited so long as they are pharmaceutically acceptable anion exchange resins. Examples include the anion exchange resins having cholesterol lowering activities which are disclosed in Japanese Patent Unexamined Publication (KOKAI) No. 56-150017/1981, European Patent Publication No. 98,884/A1, U.S. Pat. No. 4,912,011, and European Patent Publication No. 157,410/A1; cholestyramine resin sold by Sigma Chemical Company; colestipol (N-(2-aminoethyl)-N'- [2-[(2-aminoethyl)amino]ethyl]-1,2-ethane-diamine polymer coupled with (chloromethyl)oxirane) and the like.

According to the present invention, preferred examples include the 2-methylimidazole/epichlorohydrin copolymer disclosed in European Patent Publication No. 157,410 and cholestyramine resin. The 2-methylimidazole/epichlorohydrin copolymer (occasionally referred to as "MCI-196" in the specification below) has irregularly assembled and complicated stereostructure. The primary structure is represented by the following formula (I) and its partial structure is represented by the following formula (II):

The cholestyramine resin is a strongly basic anion exchange resin containing styrene/divinylbenzene copolymer coupled with quaternary ammonium groups. Its primary structure is represented by the following formula (III):

According to the present invention, the 2-methylimidazole/epichlorohydrin copolymer is particularly preferred.

As the medicaments of the present invention for preventive and/or therapeutic treatment of hyperphosphatemia, the aforementioned resins, per se, as being active substances, may be used. Alternatively, pharmaceutical compositions comprising the aforementioned active ingredients may preferably be prepared by using ordinarily used pharmaceutical additives and subjected to administration. Examples of such pharmaceutical compositions include tablets, capsules, subtilized granules, pills, troches, and liquids. These formulations are orally administered (including sublingual administration).

The orally available pharmaceutical compositions can be manufactured by conventional methods such as mixing, filling, compressing and the like. By using repeated formulation procedures, the active ingredient can be dispersed in a pharmaceutical composition containing a large amount of excipient. For example, tablets or capsules for the oral administration are preferably provided in unit dosage forms, and they may contain ordinarily used pharmaceutical additives such as, for example, binders, excipients, diluents, compressing agents, lubricants, disintegrating agents, colorants, flavoring agents, and moistening agents. Tablets may be manufactured as coated tablets by using coating materials according to methods well known in the art.

Examples of preferred excipients include cellulose, mannitol, and lactose, and disintegrating agents such as starch, polyvinylpyrrolidone, sodium starch glycolate and the like, lubricants such as sodium laurylsulfate and the like can be used as pharmaceutical additives. Orally available liquid pharmaceutical compositions may be provided, for example, in the forms of aqueous or oil suspensions, solutions, emulsions, syrups, elixirs and the like, or in the form of dry pharmaceutical compositions which can be redissolved in water or a suitable medium before use.

Such liquid compositions may contain commonly used additives which include, for example, precipitation preventing agents such as sorbitol, syrup, methyl cellulose, gelatin, hydroxyethylcellulose, carboxymethylcellulose, aluminum stearate gel, or hydrogenated edible fat; emulsifiers such as lecithin, sorbitan monooleate, or gum arabiacum; oily esters such as almond oil, refined coconut oil, or glycerin esters; non-aqueous mediums such as propylene glycol, or ethyl alcohol (edible oil may also be used); preservatives such as methyl ester, ethyl ester, or propyl ester of p-hydroxybenzoic acid, or sorbic acid; and optionally ordinarily used flavoring agents.

The pharmaceutical compositions for oral administration, for example, in the forms of tablets, capsules, or subtilized granules generally contain 5 to 95% by weight, preferably 25 to 90% by weight of the active ingredient.

The medicament of the present invention is useful for preventive and/or therapeutic treatment of hyperphosphatemia caused by diseases relating to renal dysfunction. Among them, the medicament is particularly useful for preventive and/or therapeutic treatment of hyperphosphatemia accompanied with renal dysfunction. Dose of the preventive and/or therapeutic medicament of the present invention may appropriately be chosen depending on age, clinical conditions, and body weight of a patient, and the severity of a diseases of a patient, the sort of and frequency of therapy or treatment simultaneously applied, the nature of desired effects and the like. In general, 1 to 60 g as the amount of the active ingredient can be administered per day for an adult and the daily dose may be administered at one time or several times a day.

The medicament of the present invention for preventive and/or therapeutic treatment of hyperphosphatemia reduces blood phosphate concentration and urinary phosphate excretion. Accordingly, the medicament is expected to have preventive and therapeutic effect on renal dysfunction, chronic renal failure, dialysis, hypocalcemia, PTH excess secretion, depression of vitamin D activation, or heterotopic calcification which are expected to be caused by hyperphosphatemia. Furthermore, the medicament of the present invention for preventive and/or therapeutic treatment of hyperphosphatemia is expected to have preventive and therapeutic effect on PTH increase due to hyperphosphatemia, secondary hyperparathyreosis through vitamin D reduction, renal osteoparatrophy, uremia, central and peripheral nervous disorders, anemia, myocardial disorders, hyperlipidemia, carbohydrate metabolic disorders, itch, dermal ischemic ulcer, tendon rupture, genital dysfunction, myopathy, growth retardation, cardiac conduction disturbance, pulmonary inflation disorder, arterial sclerosis, and immune deficiency.

EXAMPLES

The present invention will be more specifically explained by referring to the following examples. However, the present invention is not limited to these examples. MCI-196 used was prepared according to the method of Preparation Example 8 disclosed in European Patent Publication No. 157,410 and cholestyramine was purchased from Sigma Chemical Company. Examples 1, 2, and 3 were carried out according to the method described in Helen M. Burt et al., Journal of Pharmaceutical Science, Vol. 76, No.5 (1987), Chem. Pharm. Bull., Vol. 37, No. 7, 1936–1938 (1989). Example 4 was carried out according to the method described in American Journal of Kidney Diseases, Vol. 25, No. 6, 910–917 (1995) and Miner Electrolyte Metab., Vol. 17, 160–165 (1991).

Example 1
Measurement of Association Constant and Association Capacity Between Phosphate and Ion Exchange Resin MCI-196 or cholestyramine resin was added to an aqueous solution of 2, 3 or 4 mM $NaH_2PO_4$, at the concentration of 1 mg/ml and pH of the solution was adjusted to 7.2 with sodium hydroxide. The solution was stirred at 37° C. for 1 hour. The resin was removed using a filter and phosphate which had not bound to the resin was measured by using an inorganic phosphate measuring reagent (PiSET, Yatoron).

Figure 1:
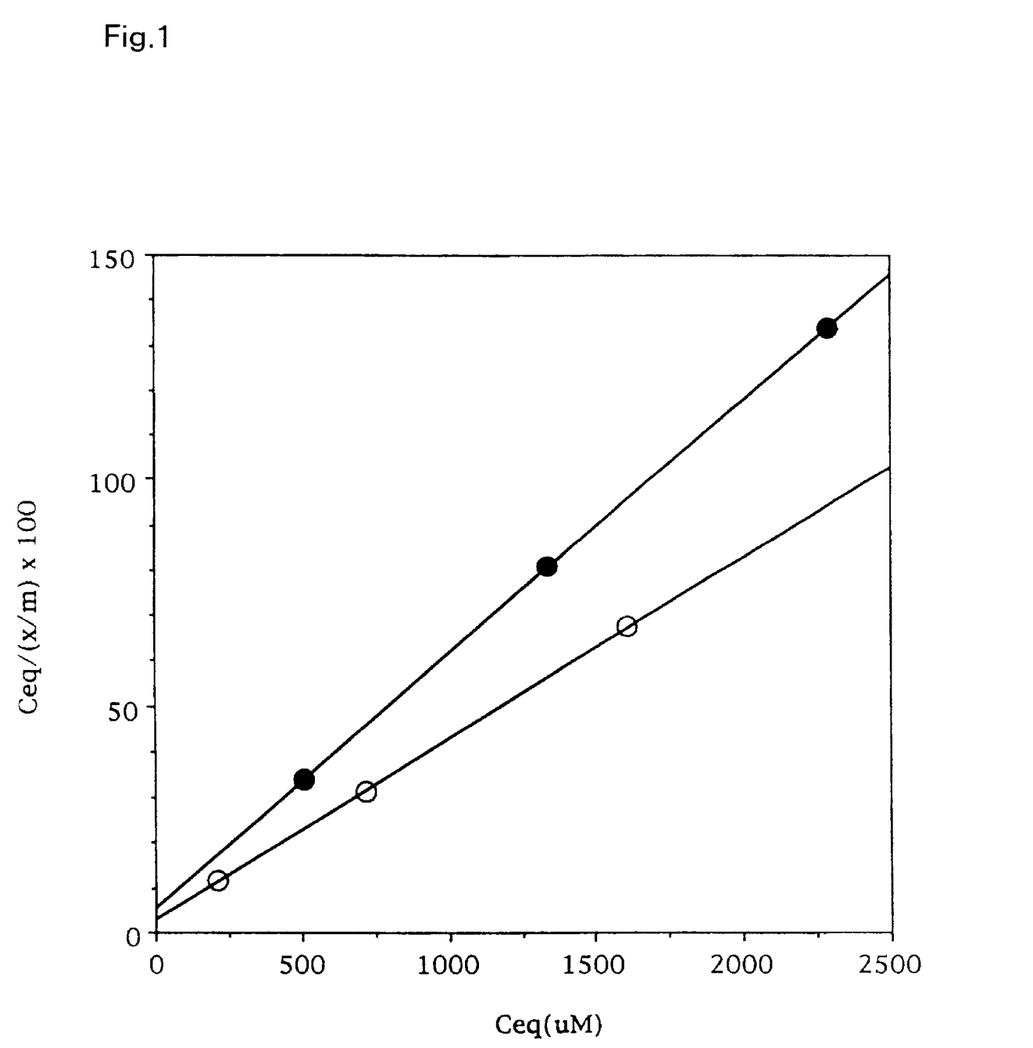
FIG. 1 shows the association constant and the association capacity (Langmuir equation) between phosphate and the ion exchange resin according to Example 1 of the present invention.

The results obtained by applying the measured phosphate concentrations to the Langmuir equation: $Ceq/(x/m)=Ceq/k2+1/k1k2$ (Ceq: phosphate concentration not bound to the resin; x: phosphate concentration bound to the resin: m: the amount of resin; $1/k2$: inclination; $1/k1k2$: intercept) are shown in FIG. 1. In the figure, ● indicates the results obtained by MCI-196 and ○ indicates the results obtained by cholestyramine resin. Association constants (k1) and association capacities (k2) calculated from the inclinations and the intercepts of the straight lines are shown in Table 1.

TABLE 1

|  | Association constant (l/m mole) | Association capacity (m mole/g) |
| --- | --- | --- |
| MCI-196 | 12.3 | 2.52 |
| Cholestyramine resin | 10.1 | 1.78 |

It is apparent from the results shown in Table 1 that each of MCI-196 and cholestyramine resin had high association constant and association capacity. In particular, MCI-196 had both of higher association constant and higher association capacity compared to the cholestyramine resin.

Example 2
Measurement of Binding Time Between Phosphate and Ion Exchange Resin

Figure 2:
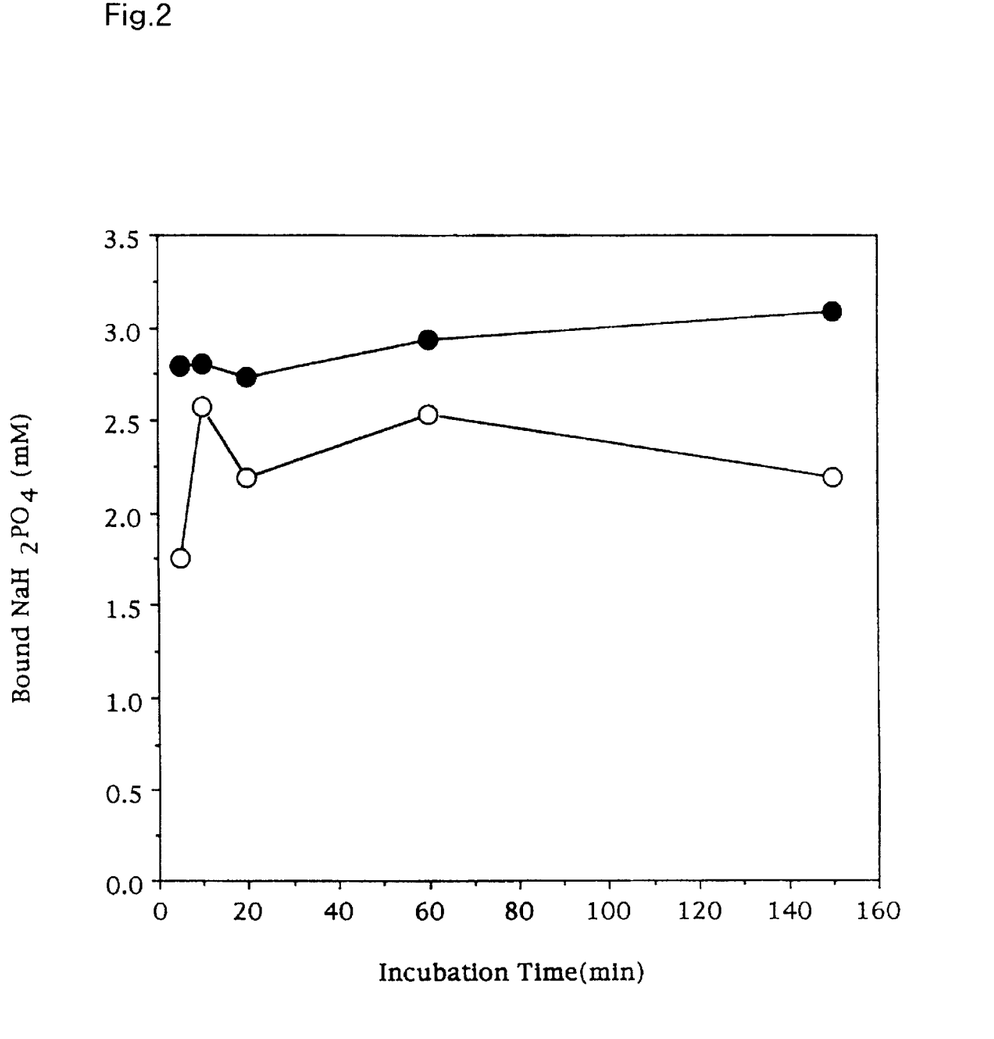
FIG. 2 shows the change of binding between phosphate and the ion exchange resin according to Example 2 of the present invention.

MCI-196 or cholestyramine resin was added to an aqueous solution of 7 mM $NaH_2PO_4$, at a concentration of 1 mg/ml and the mixture was incubated at 37° C. 5, 10, 20, and 150 minutes after the addition, the mixture was centrifuged to precipitate the resin and the phosphate in the supernatant which had not bound to the resin was measured in the same manner as Example 1. Results are summarized in FIG. 2. In the figure, ● indicates the results of MCI-196 and ○ indicates the result of cholestyramine resin. The binding of phosphate was immediately reached to equilibrium by each of MCI-196 and cholestyramine resin. In particular, a period of time up to the equilibrium by MCI-196 was shorter than that by cholestyramine resin.

Figure 3:
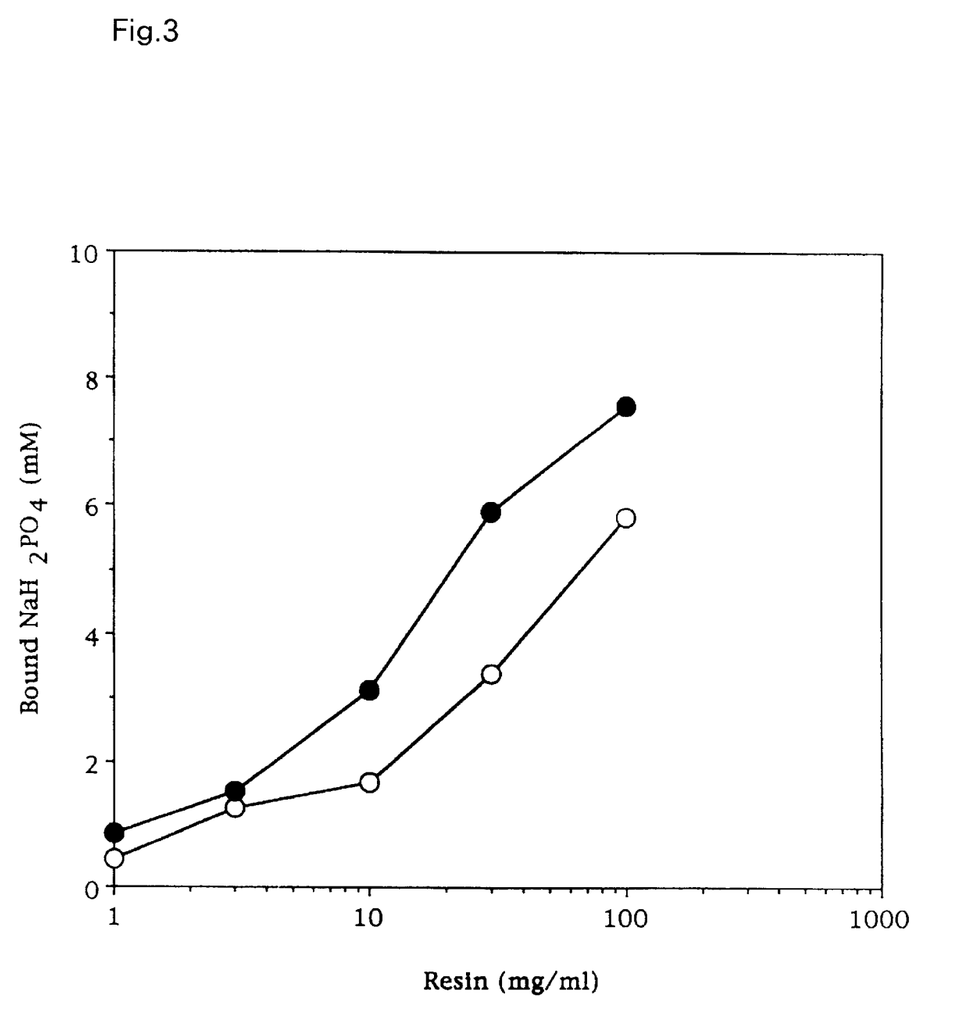
FIG. 3 shows the binding between phosphate and the ion exchange resin in the presence of other ions according to Example 3 of the present invention.

Example 3
Test of Binding Between Phosphate and Ion Exchange Resin in a Solution in the Presence of Other Ions In view of the ionic composition of intestinal juice, MCI-196 or cholestyramine resin was added at a concentration of 1, 3, 10, 30 or 100 mg/ml to an aqueous solution of 80 mM NaCl, 30 mM $Na_2CO_3$, 5 mM taurocholic acid, 10 mM oleic acid and 10 mM $NaH_2PO_4$, and the solution was incubated at 37° C. for 1 hour. Then, the resin was removed using a filter and the phosphate in the supernatant was measured according to the method described above. Results are shown in FIG. 3. In the figure, ● indicates the results of MCI-196 and ○ indicates the results of cholestyramine resin. By increasing the concentrations of both of the resins, the amounts of bound phosphate were increased. In particular, higher ratio of phosphate binding was observed with MCI-196 compared to cholestyramine resin.

Figure 4:
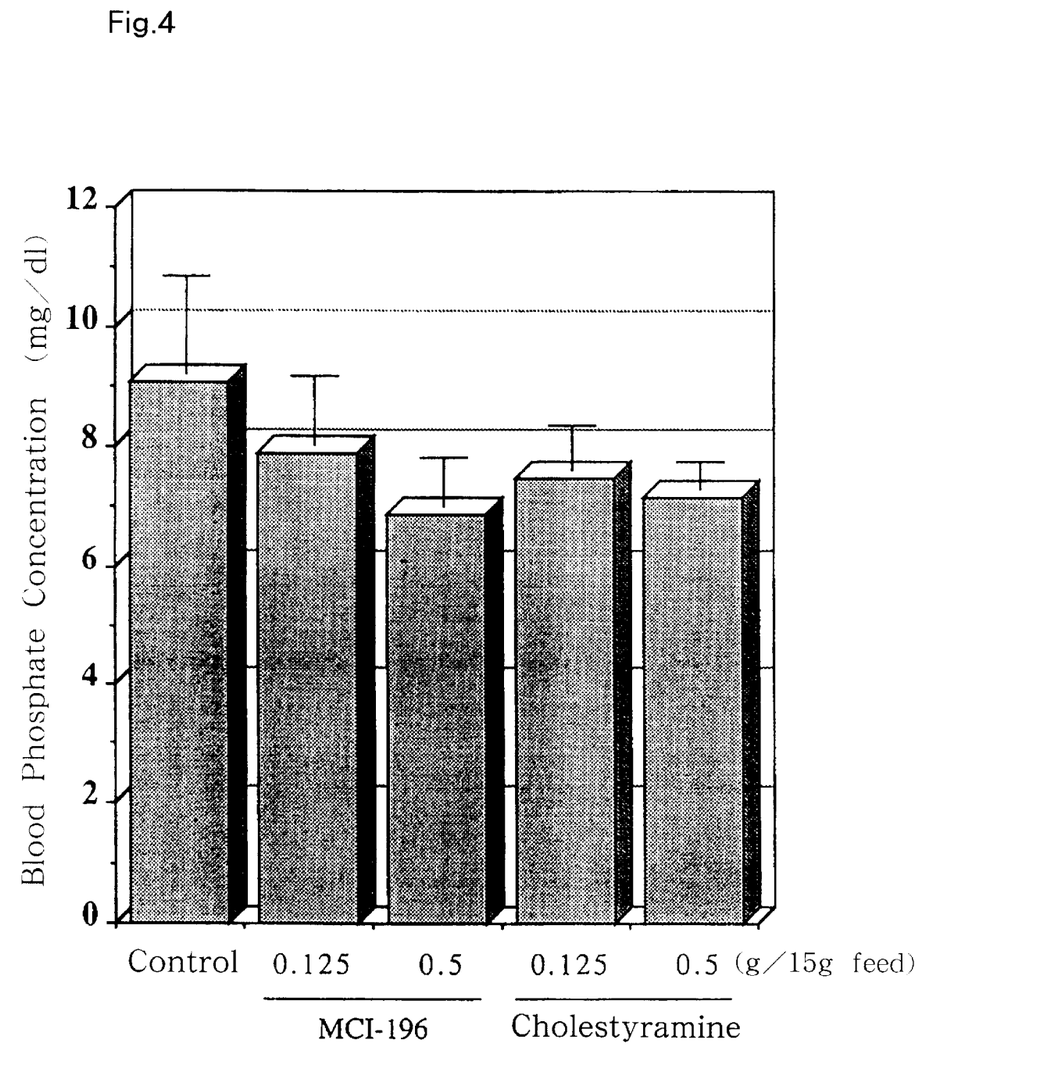
FIG. 4 shows the blood phosphate concentration after the treatment with the medicament according to Example 4 of the present invention.
Figure 5:
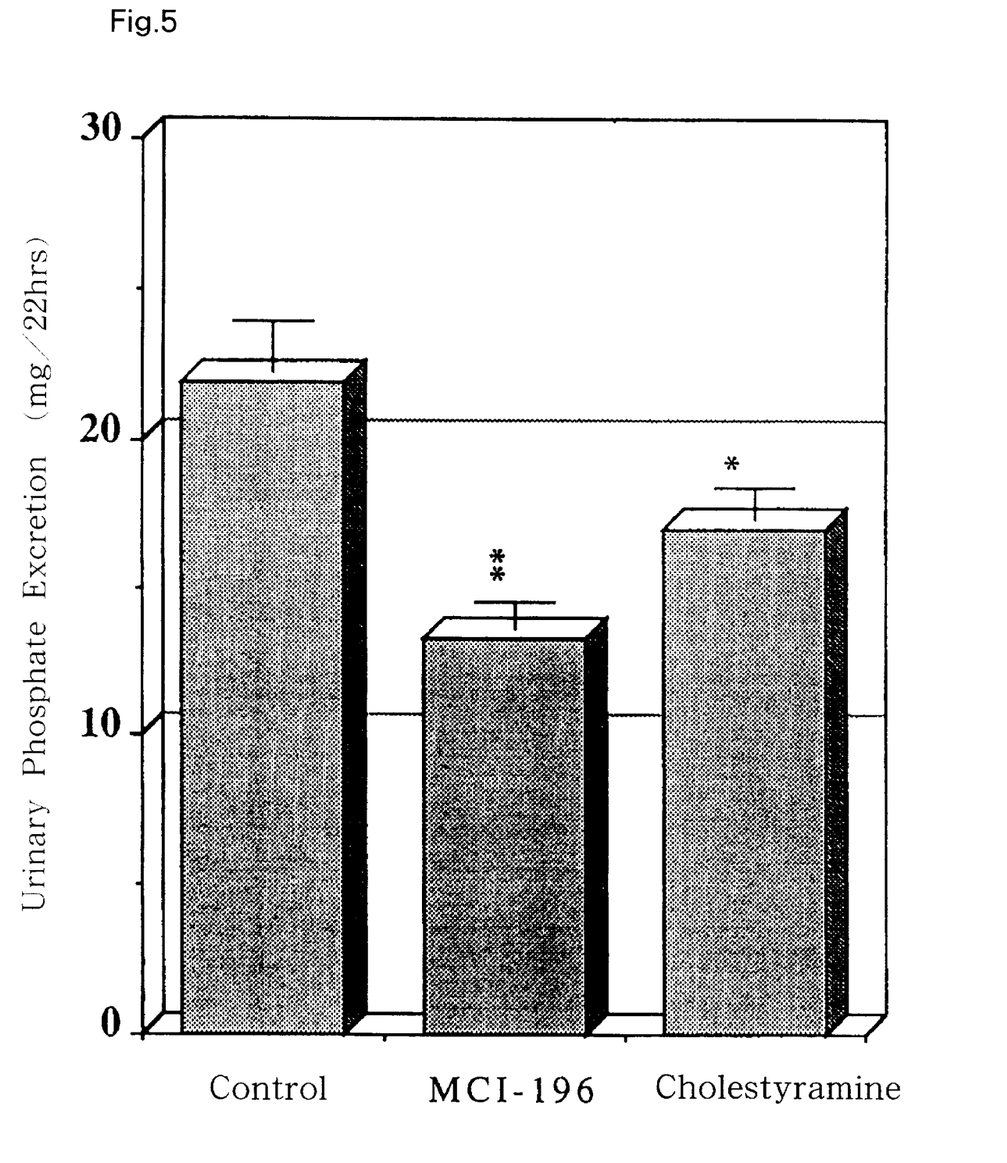
FIG. 5 shows the urinary excretion after the treatment with the medicament according to Example 4 of the present invention. In the figure, symbols * and ** represent significant differences as compared to the control ($p<0.05$ and $p<0.01$, respectively).

Example 4
Effects of Ion Exchange Resin on Blood and Urinary Phosphate Concentration in Normal Rat 6-week old Wistar male rats were administered with MCI-196 or cholestyramine by mixing the resin in feed. MF (Oriental Yeast) was used as powder feed for rat. The administration dose of MCI-196 was 0.125 or 0.5 g content per 15 g of the feed. Blood was collected from caudal vein before administration and 14 days after the administration, and blood phosphate concentrations were measured using an inorganic phosphate measuring reagent (PiSET Yatoron). For the rats given the higher dose, blood was collected from caudal vein 14 days after the administration and then urine was collected for 22 hours under starvation. Urinary phosphate concentration was measured using inorganic phosphate measuring reagent (PiSET Yatoron). Each group consisting of 9 rats was subjected to the experiment. Results are shown in FIGS. 4 and 5. In both of the groups administered with resins, dose dependent decreases of blood phosphate and urinary phosphate excretion were observed. In particular, significant decrease of urinary phosphate excretion by MCI-196 was observed, which revealed that MCI-196 has more potent reducing effect compared to cholestyramine resin.

Figure 6:
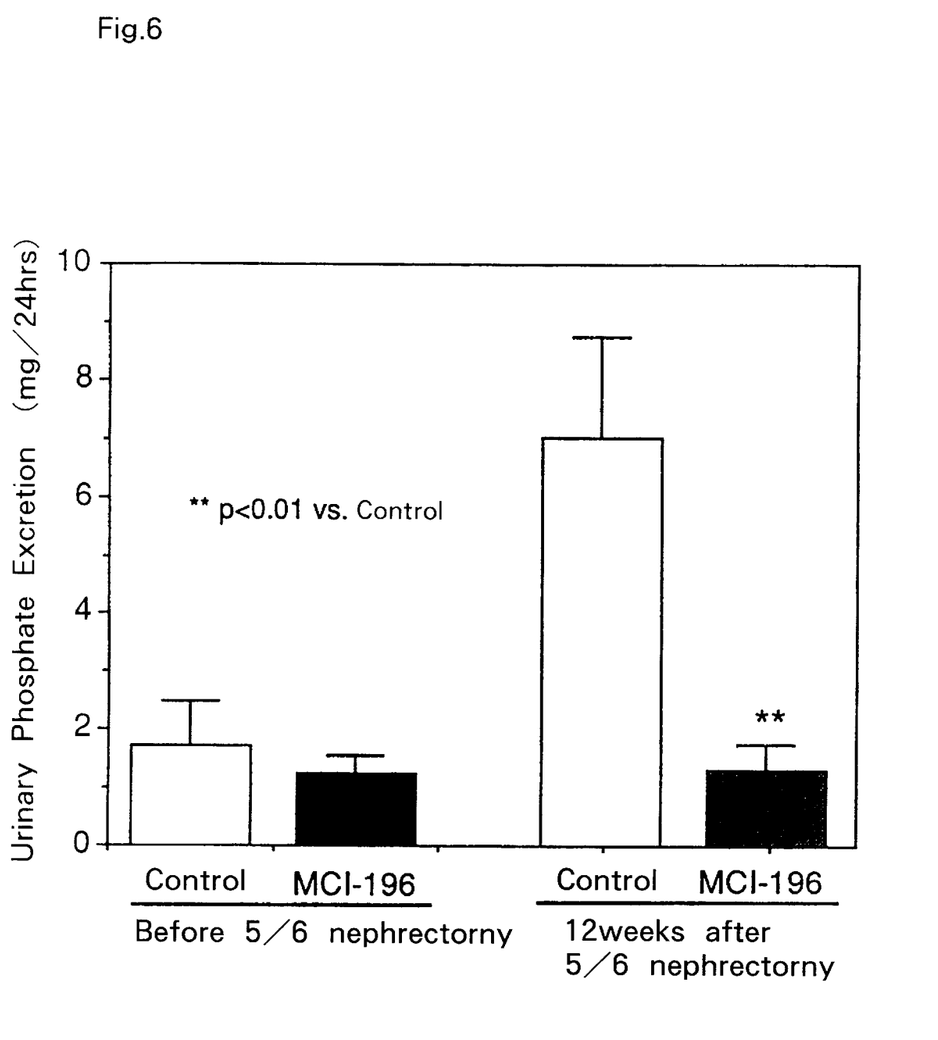
FIG. 6 shows the urinary phosphate concentration of rats subjected to 5/6 nephrectomy before and after the treatment with the medicament according to Example 5 of the present invention. In the figure, symbol ** represents significant differences as compared to the control ($p<0.01$).
Figure 7:
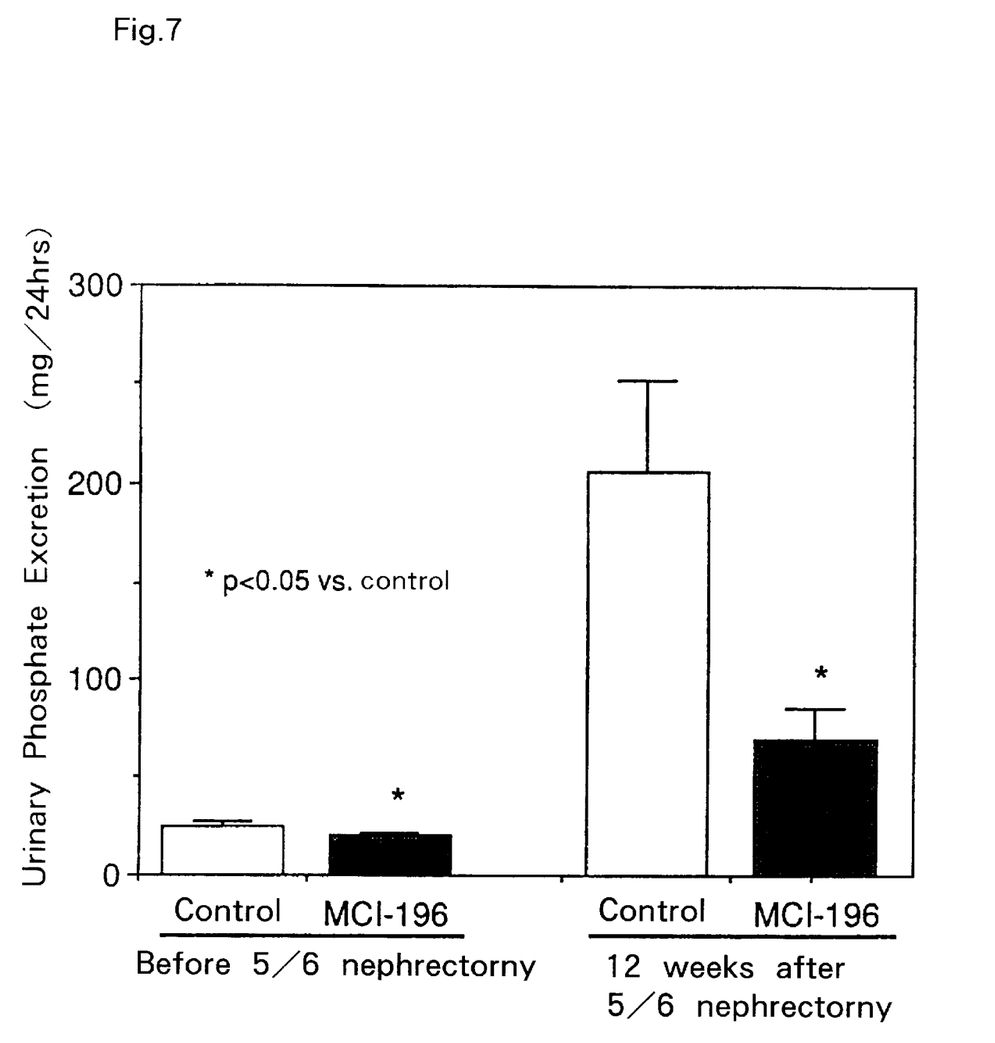
FIG. 7 shows the urinary protein excretion of rats subjected to 5/6 nephrectomy before and after the treatment with the medicament according to Example 5 of the present invention. In the figure, symbol * represents significant differences as compared to the control ($p<0.05$).

Example 5
Effect of Ion Exchange Resin on Urinary Phosphate Concentration and Renal Function of Rats Subjected to 5/6 Nephrectomy Rats of 5/6 nephrectomy were prepared using 9-week old Wistar male rats. 2/3 of the left kidney was removed, and the right kidney was removed 1 week after the operation. After one week, administration of MCI-196 mixed in feed was started. Rats of the control group were fed with normal feed. MF (Oriental Yeast) was used as the powder feed for rat. The administration dose of MCI-196 was 0.3 g content per 15 g of the feed (2%). Before the nephrectomy and 12 weeks after the nephrectomy, urine was collected for 24 hours and urinary phosphate concentration was measured using inorganic phosphate measuring reagent (PiSET Yatoron). Urinary protein concentration was also measured using a protein assay regent (Protein Assay Kit, Bio-lad). Each group consisting of 9 rats was subjected to the experiment. Results are shown in FIG. 6 and FIG. 7.

Twelve weeks after the 5/6 nephrectomy, no increase of blood phosphate concentration was observed. In the group fed with normal feed, increase of urinary phosphate excretion was observed, whereas the group administered with MCI-196 exhibited no increase of urinary phosphate excretion. In addition, the group fed with normal feed showed marked increase of urinary protein excretion, which revealed apparent deterioration of renal functions. Whereas, in the group administered with MCI-196, the increase of urinary protein excretion was significantly suppressed and improvement of renal function was observed

What is claimed is:

1. A method for the prevention or therapeutic treatment of hyperphosphatemia which comprises administering to a patient in need of such treatment an effective amount of 2-methylimidazole/epichlorohydrin copolymer sufficient to lower blood phosphate concentration or reduce urinary phosphate excretion.

2. A method according to claim 1 wherein the amount of copolymer is based on the lowering effect of the copolymer on blood phosphate concentration.

3. A method according to claim 1 wherein the amount of copolymer is based on the reducing effect of the copolymer on urinary phosphate excretion.

4. A method according to claim 1, wherein the copolymer is administered orally.

* * * * *